(12) United States Patent
Weiss et al.

(10) Patent No.: US 6,221,073 B1
(45) Date of Patent: Apr. 24, 2001

(54) WRIST FUSION APPARATUS AND METHOD

(75) Inventors: Arnold-Peter C. Weiss, Barrington, RI (US); Michael S. Collins, San Diego, CA (US)

(73) Assignee: Kinetikos Medical, Inc., San Diego, CA (US)

( * ) Notice: Subject to any disclaimer, the term of this patent is extended or adjusted under 35 U.S.C. 154(b) by 0 days.

(21) Appl. No.: 09/378,312

(22) Filed: Aug. 20, 1999

(51) Int. Cl.[7] .................................................. A61B 17/56
(52) U.S. Cl. .................................. 606/60; 606/69; 606/70
(58) Field of Search ............................ 606/60, 61, 69, 606/70, 71, 72, 73

(56) References Cited

U.S. PATENT DOCUMENTS

| 4,565,193 | * | 1/1986 | Streli | 606/60 |
| 4,867,144 | * | 9/1989 | Karas et al. | 606/60 |
| 5,197,966 | * | 3/1993 | Sommerkamp | 606/69 |
| 5,718,705 | * | 2/1998 | Sammarco | 606/69 |
| 5,853,413 | * | 12/1998 | Carter et al. | 606/69 |

* cited by examiner

Primary Examiner—Pedro Philogene
(74) Attorney, Agent, or Firm—Jenkins & Wilson, P.A.

(57) ABSTRACT

A wrist fusion apparatus and method for attachment to and positioning at least one carpus area bone relative to a radius bone without an attachment to a metacarpal bone. The wrist fusion apparatus includes an elongated plate with a bottom and top side and with a proximal portion for positioning an attachment to a radius bone and a distal portion for positioning over and attachment to at least one carpus area of bone without extending over or attaching to a metacarpal bone. The proximal portion has a linear longitudinal axis and the distal portion is disposed along a curved longitudinal line extending from the linear longitudinal axis of the approximal portion. The plate includes fastener holes defined therethrough for receiving bone fasteners.

9 Claims, 4 Drawing Sheets

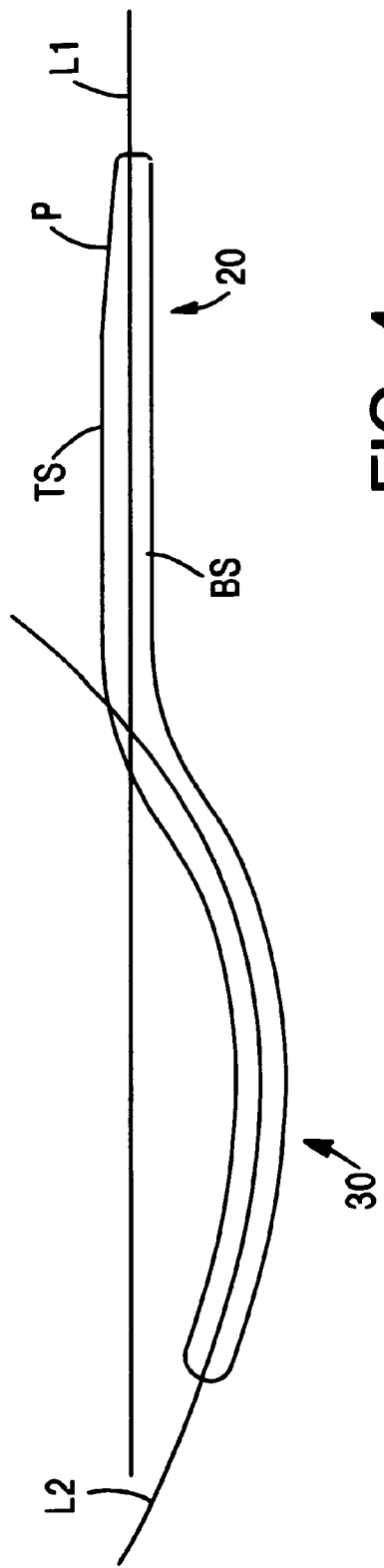
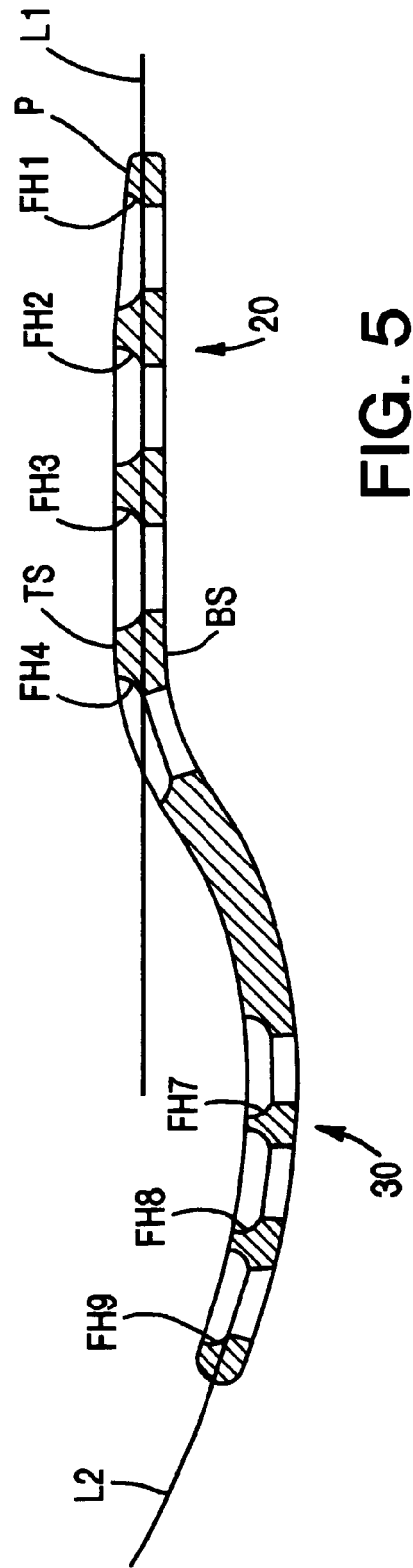

WRIST FUSION APPARATUS AND METHOD

TECHNICAL FIELD

The present invention relates generally to orthopaedic bone apparatuses and methods, and more particularly, to an anatomical wrist fusion plate apparatus and method.

BACKGROUND ART

As can be appreciated by those of skill in the art, it is common for a wrist fusion apparatus such as a plate to be used in arthrodesis to fuse bones of the wrist area of a patient in a desired orientation. A variety of configurations and designs of wrist fusion plates exist within the prior art for utilization in this manner.

It is common for some types of wrist fusion apparatuses to extend typically from the radius to a metacarpal, such as the third metacarpal, of the hand for utilization in wrist fusion. Wrist fusion apparatuses of this variety are typically fastened both to the radius and to the third metacarpal by bone screws, and wrist fusion apparatuses of this variety also therefore overlie the carpus area and the bones of the carpus area which are positioned between the radius and the metacarpal bones. As known to those of skill in the art, bone grafts can be packed between the radius, the carpus area bones, and the metacarpals after such a wrist fusion plate is in place, and the bone grafts typically will bond with the adjacent bones in order to create a fused bone mass at the wrist joint.

U.S. Pat. No. 5,853,413 to Carter et al. discloses such a wrist fusion apparatus in the form of a plate configured to extend over the carpus area and to position at least one metacarpal relative to the radius. A saddle portion is included in the wrist fusion plate and is placed over the carpus area. A proximal end extends from the saddle portion and is attachable to the radius, while a distal end extends from the saddle portion and is attachable to one of the metacarpals. The proximal end extending from the saddle portion defines a first longitudinal axis, and the distal end extending from the saddle portion defines a second longitudinal axis wherein the first and second longitudinal axes are not actually aligned in a medial-lateral direction.

Generally, the use of a dorsal wrist fusion plate is indicated in patients with post-traumatic or degenerative wrist arthritis, conditions involving significant loss of bone substance, and failed total and partial wrist arthrodesis. Wrist arthrodesis can also be successfully utilized in patients with complex fractures of the wrist. A fusion plate can be utilized in patients with rheumatoid arthritis, although simpler stabilization techniques are currently fairly predictable. Contraindications to utilizing a metacarpal sparing total wrist fusion plate involve severe carpal bone loss requiring stabilization to the metacarpal to maintain alignment and stability and evidence of active ongoing infection at the time of the surgical procedure.

Wrist fusion plate apparatuses and methods such as that disclosed in Carter et al. require attachment of a portion of the wrist fusion plate to one or more of the metacarpals of the hand. Unfortunately, this feature suffers various undesirable disadvantages, such as a high propensity for the development of extensor tendinitis at the prominent distal end of the plate necessitating removal of the plate and a second surgical procedure.

Despite the prior art wrist fusion apparatuses and methods, there remains much room for improvement in the art, particularly for a wrist fusion apparatus and method which can be used for fusing wrist bones by attachment to a radius and attachment to one or more carpus area bones without attachment to a metacarpal.

DISCLOSURE OF THE INVENTION

The present invention provides a novel wrist fusion apparatus and method for fusing wrist bones by attachment to a radius and attachment to one or more carpus area bones without attachment to a metacarpal. The wrist fusion apparatus comprises an elongated plate having a bottom side for at least partially contacting bone and an opposite top side. The plate has a proximal portion for positioning over and attachment to a radius bone and a distal portion for positioning over and attachment to at least one carpus area bone without extending over or attaching to a metacarpal bone. The proximal portion of the plate has a substantially linear longitudinal axis, and the distal portion of the plate has a curved longitudinal axis extending from the longitudinal axis of said proximal portion.

The plate defines a plurality of holes therethrough wherein the proximal portion defines at least one hole for positioning over a radius bone and the distal portion defines at least one hole for positioning over at least one carpus area bone. The plate can be positioned such that the proximal portion hole is over and can be used for attachment of the plate to a radius bone while the distal portion hole is positioned over and can be used for attachment of the plate to at least one carpus area bone for wrist fusion by the wrist fusion apparatus without attachment of the plate to a metacarpal bone.

It is therefore an object of the present invention to provide a novel wrist fusion apparatus and method for fusing wrist bones by attachment to a radius and attachment to one or more carpus area bones.

It is also an object of the present invention to provide a wrist fusion apparatus and method for utilization in fusing wrist bones without attachment to a metacarpal.

It is a further object of the present invention to provide a wrist fusion apparatus and method wherein the wrist fusion apparatus can effectively and easily be surgically placed into position and which can be effectively and easily utilized for wrist fusion.

Some of the objects of the invention having been stated hereinabove, other objects, in whole or in part, will become evident as the description proceeds, when taken in connection with the accompanying drawings as best described hereinbelow.

BRIEF DESCRIPTION OF THE DRAWINGS

FIG. 4 of the drawings is an elevated side view of the wrist fusion apparatus according to the present invention; and FIG. 5 of the drawings is a cross-sectional view of the wrist fusion apparatus according to the present invention drawn along line 5—5 of FIG. 2 of the drawings.

DETAILED DESCRIPTION OF THE INVENTION

Referring now to the various figures of drawings, a wrist fusion apparatus generally designated 10 is illustrated and can be used to fuse wrist bones as described herein without attachment to a metacarpal.

In a preferred embodiment, wrist fusion apparatus 10 comprises an elongated plate P which can be constructed of any suitable material for purposes as taught herein, but in a preferred embodiment is constructed of stainless steel. Plate P is suitably anatomically designed and adapted for positioning over an attachment to a radius as well as one or more carpus area of bones for utilization in fusing wrist bones as can be appreciated by those of skill in the art. While the dimensions and structure of plate P can vary, plate P in a preferred embodiment has a length of approximately three (3) inches, a width of approximately one-half (½) inch, and a thickness of approximately one-eighth (⅛) inch.

Figure 1A:
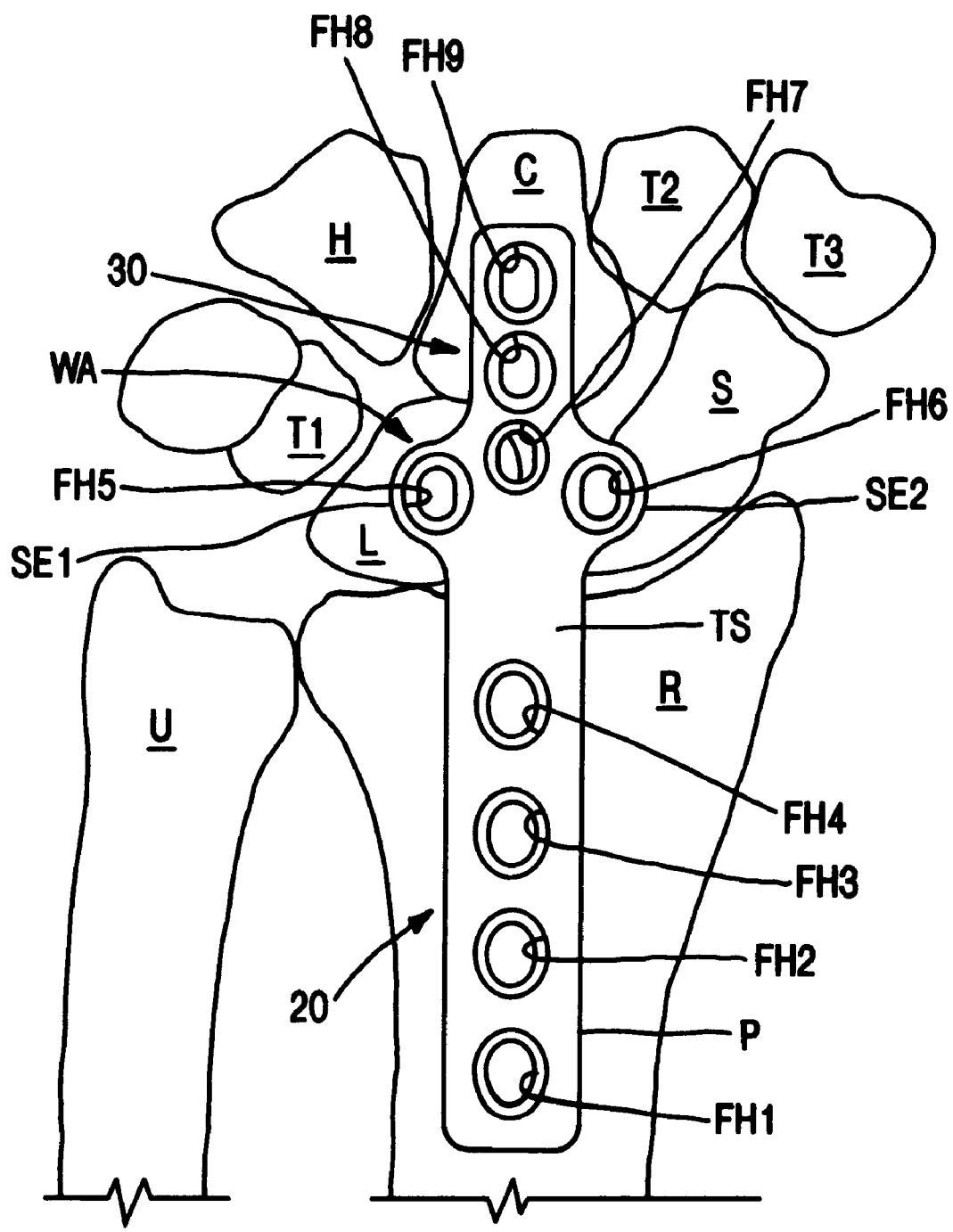
FIG. 1A of the drawings is a top plan view of the wrist fusion apparatus according to the present invention positioned in place over a radius and a plurality of carpus area bones.
Figure 1B:
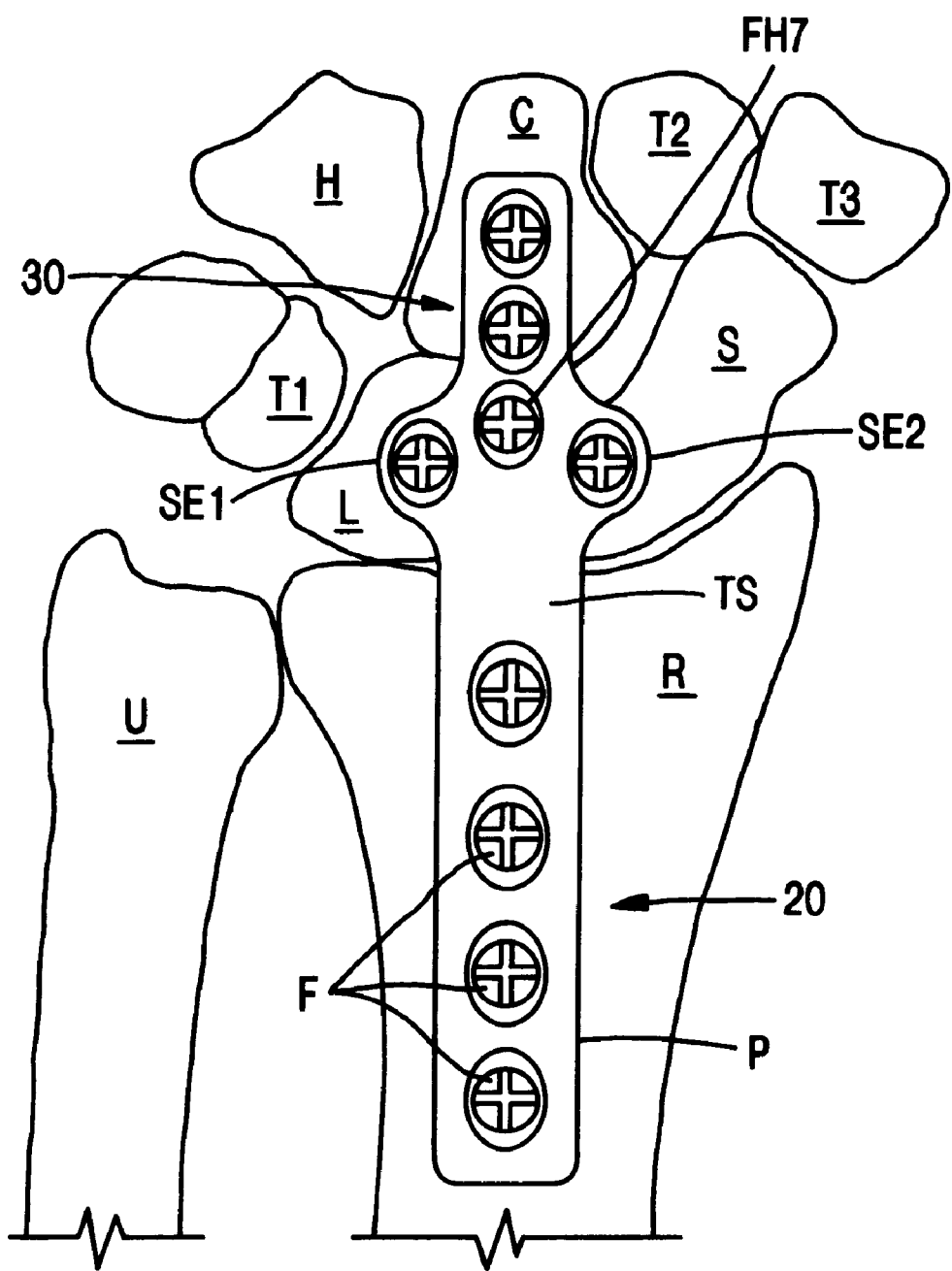
FIG. 1B of the drawings is identical to FIG. 1A but illustrating the wrist fusion apparatus according to the present invention secured in place by a plurality of bone screws utilized as fasteners.
Figure 2:
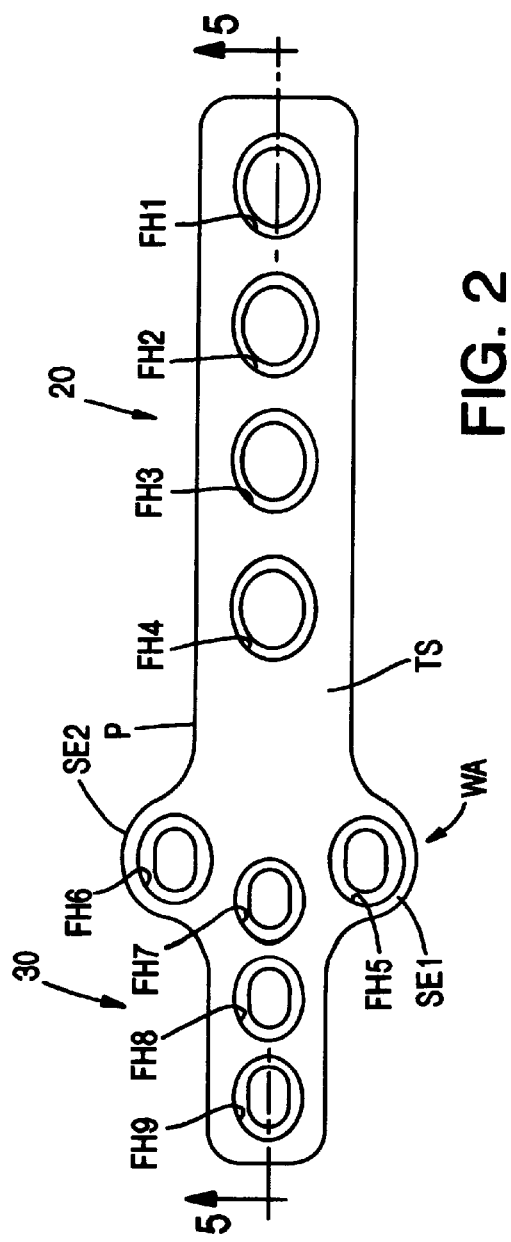
FIG. 2 of the drawings is an isolated top plan view of the wrist fusion apparatus according to the present invention.
Figure 3:
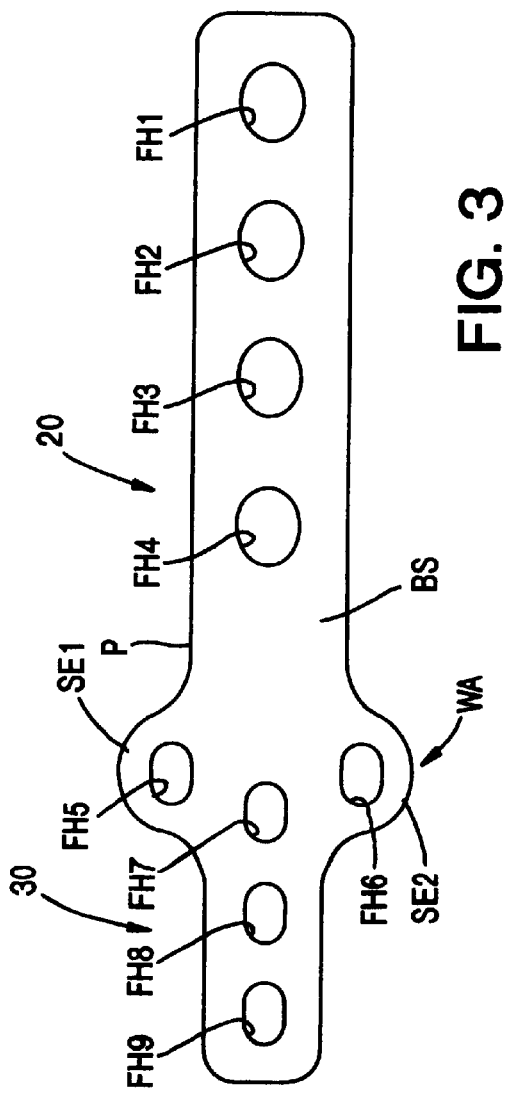
FIG. 3 of the drawings is an isolated bottom plan view of the wrist fusion apparatus according to the present invention.

As illustrated in FIG. 1A of the drawings, plate P is shown in its preferred position for utilization in wrist fusion as a portion of plate P is positioned over a radius R while another portion of plate P is positioned over a plurality of carpus area bones. More specifically, proximal portion generally designated 20 of plate P extends and is positioned over radius R, and distal portion generally designated 30 of plate P is positioned over a plurality of carpus area bones, which as shown in FIG. 1A of the drawings comprise a lunate L, a capitate C, and a scaphoid S. While FIG. 1A of the drawings illustrates a preferred position for utilization in wrist fusion, it is envisioned in accordance with this invention that plate P can extend and be positioned over other suitable combinations of wrist area bones as desirable wherein such combinations could include, for example, bones such as an ulna U, a triquetrium T1, a hamate H, a trapezoid T2, and a trapezium T3. Plate P has a topside TS which is best illustrated in FIG. 1A, 1B and 2 of the drawings, and plate P also has an opposite bottom side BS for at least partially contacting bone.

As illustrated in the various figures of drawings, plate P defines a plurality of fastener holes therethrough which are disposed in selected positions across the length and width of plate P and adapted for receiving a suitable bone fastener such as a bone screw. While it is envisioned according to this invention that a plurality of fastener holes can be defined through plate P in any suitable configuration for utilization in wrist fusion, a preferred configuration of fastener holes defined through plate P includes fastener holes FH1, FH2, FH3, and FH4 centrally defined through plate P on its proximal portion 20 as best illustrated in FIGS. 1A, 2 and 5. Fastener holes FH1–FH4 are adapted for positioning over radius R as illustrated best in FIG. 1A of the drawings. Also in the preferred embodiment as illustrated in the various figures of drawings, plate P defines fastener holes FH5, FH6, FH7, FH8, and FH9 through plate P in distal portion 30 of plate P.

Fastener holes FH5–FH9 are in this preferred embodiment positioned and configured so as to be positioned over a plurality of carpus area bones. More particularly, fastener hole FH5 is positioned over lunate L, while fastener hole FH6 is positioned and configured so as to be over scaphoid S. Fastener holes FH7, FH8 and FH9 are positioned and configured so as to be over capitate C as shown in FIG. 1A. Fastener holes FH1–FH9 defined through plate P can be of various suitable sizes and shapes and preferably are all countersunk for receiving at least one bone screw. FIG. 1B of the drawings illustrates plate P fastened in its preferred position for utilization in wrist fusion as all fastener holes FH1–FH9 have fasteners F received therethrough, which in the preferred embodiment are bone screws for attaching plate P in position against the underlying bones.

As best illustrated in FIGS. 1A, 1B, 2 and 3 of the drawings, plate P can be said to be "t" shaped in that it preferably includes a widened area generally designated WA. Widened area WA is generally part of distal portion 30 of plate P, but widened area WA does not constitute the entire distal portion 30 as the drawings clearly illustrate that the furthermost distal portion of distal portion 30 of plate P is not a widened area such as widened area WA, but rather is narrower in width and includes fastener holes FH8 and FH9. Widened area WA comprises opposing side extensions SE1 and SE2 which are generally arch-like in shape and extend from opposite sides of plate P and in opposite directions, as best illustrated in FIGS. 1A, 1B, 2 and 3 of the drawings. Fastener hole FH5 is defined at least partially through side extension SE1, and fastener hole FH6 is defined at least partially through side extension side SE2 as illustrated in the drawings, while fastener hole FH7 is positioned at least partially between fastener holes FH5 and FH6. Fastener holes FH1–FH4 and FH7–FH9 preferably are disposed along the same line on plate P.

Referring now to FIGS. 4 and 5 of the drawings, the side shape of plate P is best illustrated in its anatomical design adapted specifically for positioning over and attachment to a radius bone and one or more carpus area bones. Most or all of proximal portion 30 of plate P is planer and disposed along linear longitudinal axis L1, and the shape of plate P curves in an arcuate manner below and away from longitudinal axis L1 as proximal portion 20 transitions to distal portion 30 and is disposed along curved longitudinal line L2. An angle of between approximately zero (0) degrees and ninety (90) degrees preferably exists between longitudinal axis L1 and curved line L2. As shown in FIG. 5 of the drawings in the preferred embodiment, such curve begins along curved longitudinal line L2 approximately at fastener hole FH4. Distal portion 30 of plate P therefore is curved as compared to the planar proximal portion 20. After curving below and away from longitudinal axis L1, distal portion 30 of plate P gradually curves as it follows curved longitudinal line L2 back towards longitudinal axis L1. Distal portion 30 of plate P therefore is arcuate in shape from a side or cross sectional view as it follows curved longitudinal line L2 as illustrated in FIGS. 4 and 5.

Wrist Fusion Method

As described above, the use of a dorsal wrist fusion plate is generally indicated in patients with post-traumatic or degenerative wrist arthritis, conditions involving significant loss of bone substance, rheumatoid arthritis, and failed total and partial wrist arthrodesis. Wrist arthrodesis can also be successfully utilized in patients with complex fractures of the wrist.

The wrist fusion apparatus according to the present invention and as described above can be utilized effectively and easily for wrist fusion as described herein and as can readily be appreciated by those of skill in the art.

The method of utilizing the wrist fusion apparatus of this invention comprises initially providing anesthesia by either regional axillary block or general anesthesia. An extremity tourniquet should be utilized in the upper arm allowing exsanguination of the upper extremity prior to surgery. A longitudinal dorsal wrist incision is made from the base of the third CMC joint distally extending proximally across Lister's tubercle to a point approximately 4–5 cm proximally to Lister's tubercle. Skin and subcutaneous tissues are freed from the underlying retinaculum both radially and ulnarly. The third extensor compartment is identified and opened, and the extensor pollicus longus tendon is completely freed, transposed radially, allowing exposure to the floor of the third compartment.

An incision from the distal radius in line distally with the third compartment over the distal radius is carried out through the capsular structures between the second and fourth compartment to the third CMC joint. Capsular flaps should be raised radically and ulnarly in as thick a fashion as possible. Utilizing this technique, excellent exposure to the carpus area is obtained. Capsular flaps are then peeled proximally off the proximal radius with portions of the retinaculum exposing the distal end of the distal radius flattened out to accommodate the contour of the plate using an osteotome and/or rongeur. Utilizing a rongeur and small osteotomes, denution of the cartilage between the radius and carpal bones is undertaken specifically ensuring that cancellous bone is present at the distal radius, proximal and distal lunate, proximal and distal scaphoid, and proximal capitate. At least the dorsal one-half of the cartilage surface should be denuded to subchondral bone.

Local bone can be then be taken from the distal radius. This bone graft can later be packed into the gap or interstices between capitate C, scaphoid S-lunate L, and scaphoid S-lunate L-radius R. At least some portion, preferably approximately 1 cm bridge, of cancellous bone at the distal radius R articular surface should not be violated during the bone graft harvesting to aid in bony fusion.

Wrist fusion plate P is then suitably positioned and aligned with at least one of fastener holes FH7, FH8, and/or FH9 (preferably at least two) placed or aligned over capitate C; fastener hole FH6 aligned over the proximal portion of scaphoid S; fastener hole FH5 aligned over lunate L, and at least one or more, and preferably all, of remaining proximal fastener holes FH1–FH4 aligned over the distal portion of radius R. In the preferred embodiment, fastener holes FH7, FH8 and FH9 are aligned over capitate C. Additional shaping of the distal portion of radius R might be required to allow optimal contouring of plate P in position, and this graft can be utilized to augment that previously obtained.

After appropriate alignment, a drill bit (preferably 2.0 mm) or other suitable tool can be utilized in a sequential fashion to attach or affix suitable self-tapping screws (preferably 2.8 mm) of appropriate length to capitate C through at least one of fastener holes FH7, FH8, and/or FH9 (preferably through only fastener holes FH8 and FH9), followed by one screw each in lunate L and scaphoid S through fastener holes FH5 and FH6, respectively. Finally, a drill bit (preferably 2.5 mm) or other suitable tool can be used to place and fasten self-tapping proximal bone screws (preferably 3.5 mm) to radius R.

The wound can then be appropriately irrigated and the capsular structures repaired in a sequential fashion followed by the retinacular tissues. The EPL tendon can be left transposed. A closed suction drain can be placed if desired and the skin closed using nonabsorbable sutures. A light bulky dressing can be placed as well as a volar splint for comfort.

Postoperative protocol comprises the patient's postoperative dressing and splint being maintained for 10 to 14 days at which time it can be removed and the skin sutures taken out. A molded orthoplast splint can be fashioned or, alternatively, the patient can be placed in a short-arm light-weight fiberglass cast. The patient should maintain either splint of cast immobilization until consolidation of the fusion site is noted on follow-up radiographs. Postoperative fusion consolidation generally occurs at six to eight weeks. Patients should be encouraged to undertake early active and passive range of motion of the thumb and all four digits as well as wrist pronation/supination immediately postoperatively. Strength exercises should not be started prior to fusion consolidation, as can be appreciated by those of skill in the art.

Fixation of plate P in position as described above therefore provides desirable stability so as to allow the various bones beneath plate P to fuse properly. Although it is possible that plate P also provides some degree of compression additionally, it is not a focus of the present invention for plate P to provide compression for the bones beneath plate P. Utilizing plate P for wrist fusion is believed to eliminate complications which can typically occur with the use of conventional wrist fusion apparatuses such as wrist fusion plates used primarily for patients with post-traumatic or osteoarthritis.

It can therefore be seen that the present invention provides a novel wrist fusion apparatus and method for fusing wrist bones by attachment to a radius and attachment to one or more carpus area bones. It can also be seen that the present invention provides a wrist fusion apparatus and method for utilization in fusing wrist bones without attachment to a metacarpal. Finally, it can be understood that the present invention provides a wrist fusion apparatus and method wherein the wrist fusion apparatus can effectively and easily be surgically placed into position and which can be effectively and easily utilized for wrist fusion.

It will be understood that various details of the invention may be changed without departing from the scope of the invention. Furthermore, the foregoing description is for the purpose of illustration only, and not for the purpose of limitation, as the present invention is defined by the following, appended claims.

What is claimed is:

1. A method of fusing a wrist using a wrist fusion apparatus, said method comprising the steps of:
   (a) providing a wrist fusion apparatus comprising:
      (i) an elongated plate having a bottom side for at least partially contacting bone and an opposite top side, said plate having a proximal portion for positioning at least partially over and attachment to a radius bone and a distal portion for positioning at least partially over and attachment to at least one carpus area bone without extending over or attaching to a metacarpal bone;
      (ii) said proximal portion of said plate having a longitudinal axis, and said distal portion of said plate being disposed along a substantially curved line extending from the longitudinal axis of said proximal portion; and
      (iii) said plate defining a plurality of holes therethrough wherein said proximal portion defines at least one hole for positioning over a radius bone and said distal portion defines at least one hole for positioning over at least one carpus area bone;
   (b) positioning said proximal portion of said plate over and attaching said proximal portion to a radius bone;
   (c) positioning said distal portion of said plate over and attaching said distal portion to at least one carpus area bone without attachment to a metacarpal bone.

2. The method of claim 1 further comprising attaching said distal portion of said plate to a plurality of carpus area bones.

3. The method of claim 2 further comprising attaching said distal portion of said plate to a lunate bone, a capitate bone, and a scaphoid bone.

4. The method of claim 1 wherein said steps of paragraphs (b) and (c) are accomplished by fastening a bone screw through each of said holes.

5. The method of claim 1 wherein said steps of paragraphs (b) and (c) comprise aligning said plate such that said bottom surface of said plate is in substantial contact with bone.

6. A method of fusing a wrist using a wrist fusion apparatus, said method comprising the steps of:
  (a) providing a wrist fusion apparatus comprising:
    (i) an elongated plate having a bottom side for at least partially contacting bone and an opposite top side, said plate having a proximal portion for positioning over and attachment to a radius bone and a distal portion for positioning over and attachment to a plurality of carpus area bones without extending over or attaching to a metacarpal bone;
    (ii) said distal portion of said plate defining a widened area such that said plate is substantially "t" shaped;
    (iii) said proximal portion of said plate having a longitudinal axis, and said distal portion of said plate being disposed along a substantially curved line extending from the longitudinal axis of said proximal portion, wherein the curved line of said distal portion extends initially in a direction away from the longitudinal axis of said proximal portion and then in a direction back toward the longitudinal axis of said proximal portion; and
    (iv) said plate defining a plurality of holes therethrough wherein said proximal portion defines at least one hole for positioning over a radius bone and said distal portion defines a plurality of holes, including at least one hole positioned through said widened area, for positioning at least one hole over each of a plurality of carpus area bones;
  (b) positioning said proximal portion of said plate over and attaching said proximal portion to a radius bone by fastening a bone screw through said hole of said proximal portion to a radius bone; and
  (c) positioning said distal portion of said plate over and attaching said distal portion to a plurality of carpus area bones without attachment to a metacarpal bone by fastening a bone screw through each of said holes of said distal portion to a plurality of carpus area bones including fastening at least one bone screw to a carpus area bone through said at least one hole of said widened area.

7. The method of claim 6 wherein the step of paragraph (c) comprises fastening at least one bone screw through a hole of said distal portion to a capitate bone, fastening at least one bone screw through a hole of said distal portion to a lunate bone, and fastening at least one bone screw through a hole of said distal portion to a scaphoid bone.

8. The method of claim 7 wherein the step of paragraph (c) comprises fastening at least one bone screw through a hole of said widened area of said distal portion to a lunate bone and fastening at least one bone screw through a hole of said widened area of said distal portion to a scaphoid bone.

9. The method of claim 6 wherein said steps of paragraphs (b) and (c) comprise aligning said plate such that said bottom surface of said plate is in substantial contact with bone.

* * * * *